United States Patent [19]
Wickham

[11] Patent Number: 5,897,575
[45] Date of Patent: Apr. 27, 1999

[54] ARRHYTHMIA CLASSIFICATION SYSTEM WITH RELIABILITY INDICATION THAT ALLOWS FOR LOW QUALITY INPUT SIGNALS IN PACEMAKERS

[75] Inventor: John Wickham, Fivedock, Australia

[73] Assignee: Pacesetter, Inc., Sylmar, Calif.

[21] Appl. No.: 08/957,336

[22] Filed: Oct. 24, 1997

[51] Int. Cl.⁶ .............................. A61N 1/39; A61N 1/36
[52] U.S. Cl. .................................................. 607/4; 607/14
[58] Field of Search ............................................. 607/4, 14

[56] References Cited

U.S. PATENT DOCUMENTS

| | | |
|---|---|---|
| 4,869,252 | 9/1989 | Gilli . |
| 4,940,054 | 7/1990 | Grevis . |
| 4,960,123 | 10/1990 | Maker . |
| 5,086,772 | 2/1992 | Larnard . |
| 5,144,947 | 9/1992 | Wilson . |
| 5,395,393 | 3/1995 | Wickham . |
| 5,454,836 | 10/1995 | van der Veen et al. ............... 607/9 |
| 5,500,004 | 3/1996 | Ansourian et al. . |

*Primary Examiner*—William E. Kamm
*Assistant Examiner*—Carl H. Layno
*Attorney, Agent, or Firm*—Gottlieb, Rackman & Reisman, P.C.

[57] ABSTRACT

An implantable cardiac device wherein a reliability indicator is developed for cardiac classification based on the presence or absence of noise. If the classification is unreliable a robust therapy is applied until the cardiac condition is confirmed.

15 Claims, 5 Drawing Sheets

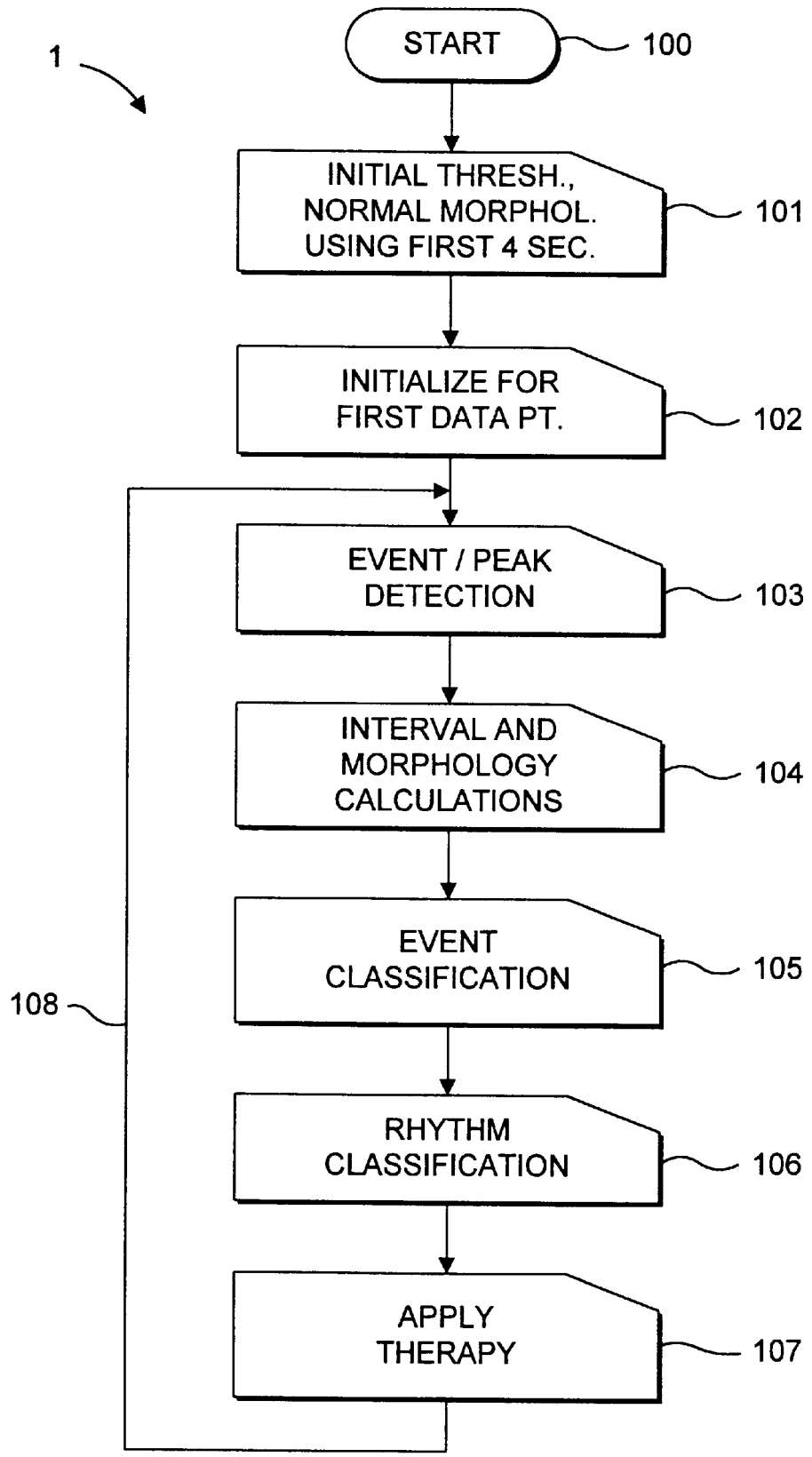
F I G. 2

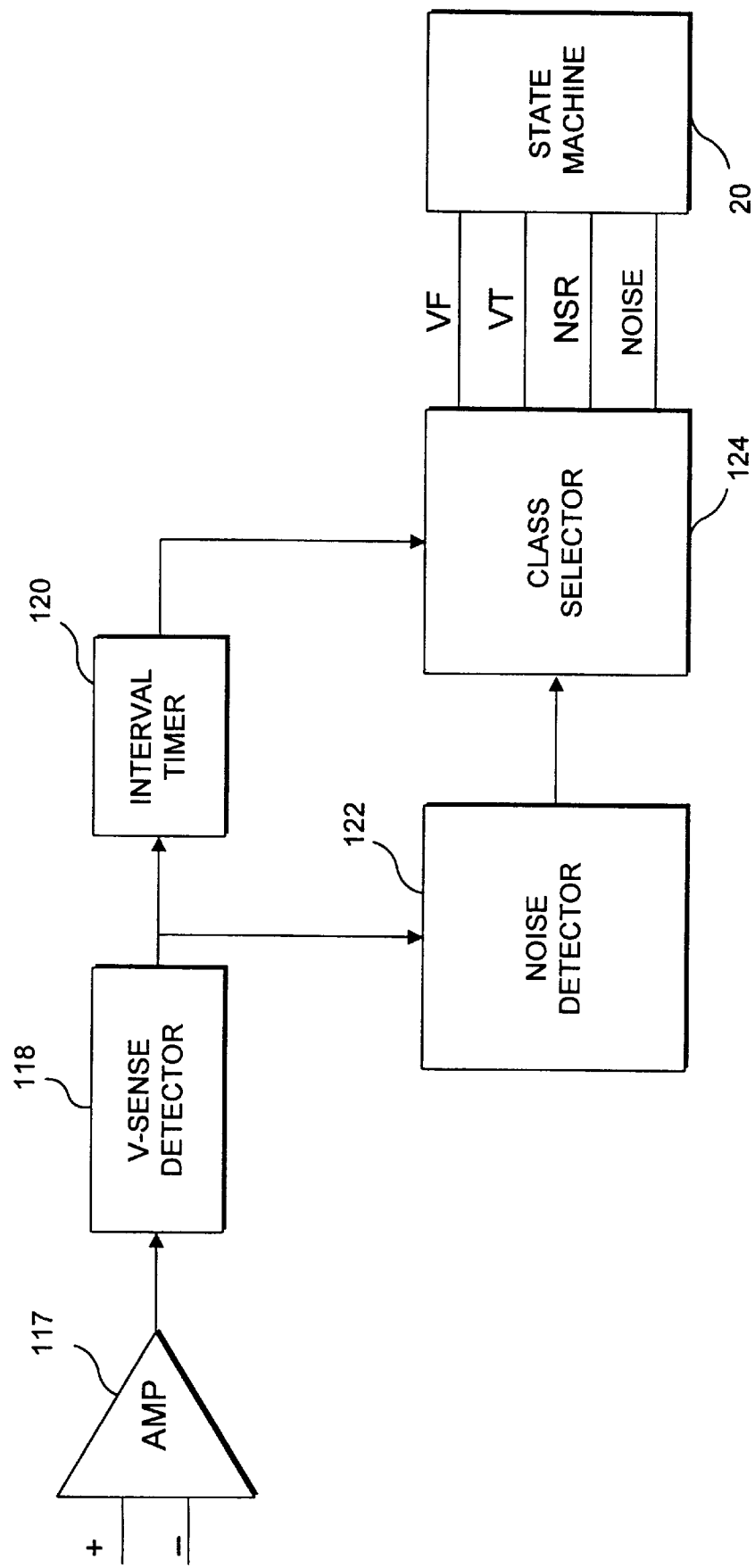
F I G. 3

ARRHYTHMIA CLASSIFICATION SYSTEM WITH RELIABILITY INDICATION THAT ALLOWS FOR LOW QUALITY INPUT SIGNALS IN PACEMAKERS

BACKGROUND OF THE INVENTION a. Field of Invention

This invention relates to cardiac pacemakers and defibrillators. More particularly, it relates to an apparatus and method for classifying cardiac rhythms and providing appropriate electrical stimulation to the heart.

b. Description of the Prior Art

If an implantable device which is to provide electrical stimulation to the heart is to be truly useful, then it must be able to sense the electrical activity of the heart, classify cardiac rhythms, and determine what electrical therapy would be most appropriate.

Various methods and apparatus have been proposed for sensing and classifying cardiac rhythms. The cardiac waveform may be monitored for determining AA, AV, VA, and VV intervals. It is also possible to monitor the morphology of the waveform. In addition, hemodynamic sensors have been used. Generally, morphology and hemodynamic sensors are used as gating functions.

The difficulty with most such classification apparatus and methods is that they are not accurate. Further, the use of morphology or hemodynamic condition as a sensing or gating function does not provide for a fine enough classification of cardiac rhythm.

U.S. Pat. No. 5,086,772 entitled Arrhythmia Control System Employing Arrhythmia Recognition Algorithm, assigned to the assignee of the present invention, utilizes an arrhythmia recognition algorithm to detect and distinguish among bradycardia, sinus rhythm, superventricular tachycardia and ventricular fibrillation, and deliver therapy in the form of electrical energy to cardiac tissue to revert selected arrhythmias and restore normal sinus rhythm. The techniques described therein are generally more accurate than most because the rhythm classification part of the method disclosed therein provides numerical outputs and rhythm categories which are not overlapping and are mutually exclusive from one another, so that there is no doubt of the rhythm category being outputted at any given time.

The difficulty with all the above techniques of heart rhythm classification is that they assume a good quality input signal that enable a reliable and consistent classification to be made. It is common for the input signal (whether it is electrical, haemodynamic or other measure of the heart's function) to be of insufficient quality for consistent and accurate classification, and thus cause these systems to deliver incorrect therapy to the patient. An example of this is with some schemes of antitachycardia pacing which require a very accurate measurement of the heart beat interval. In the situation where the heart's electrogram is such that a sufficiently accurate measurement cannot be made, it is safer to use some other form of therapy that does not require this accuracy.

OBJECTIVES AND SUMMARY OF THE INVENTION

It is an objective of the invention to provide a method and apparatus for the classification of arrhythmias which is adaptable in accordance with the quality of the signals sensed in the heart.

It is a further objective of the invention to provide a method and apparatus which selects the most appropriate therapies according to the sensed condition of the heart in combination with the measured quality or reliability of such sensing.

In accordance with the invention there is provided a cardioverting device for reverting tachycardia in a heart. The device comprises a sense amplifier for sensing ventricular waveforms of the heart; a classifier for classifying the waveforms in accordance with classification criteria; a pulse generator for generating therapy waveforms to be applied to the heart; a physiological sensor for monitoring a physiological parameter of the patient and for providing an output signal representative of said parameter; and a converter for converting said output signal so that said signal is used by said classifier to modify the classification criteria so that said generator applies an appropriate therapy waveform to the heart.

The classification criteria include cardiac rate, and the output signal modifies the rate used for classification. The physiological sensor may detect a parameter selected from the group consisting of right ventricular pressure, minute ventilation, and patient activity.

The invention is also directed to a method for reverting tachycardia in the heart of a patient comprising sensing ventricular waveforms of the heart; classifying the waveforms in accordance with classification criteria; generating therapy waveforms to be applied to the heart; monitoring a physiological parameter of the patient and providing an output signal representative of said parameter, and using said output signal to modify said classification criteria so that an appropriate waveform is applied to the heart.

Importantly, in the present invention, a signal quality indicator is also derived to indicate whether the sensed signal is reliable. This indicator is used to decide what kind of treatment should be delivered to the patient. For a reliable sensed signal, standard rhythm classification and therapy may be used. However, for a poor quality signal, a more conservative approach may be used, including for example pacing at a full back rate while the pathological condition of the heart can be assessed more accurately.

BRIEF DESCRIPTION OF THE DRAWINGS

Further objects, features and advantages of the invention will become apparent upon consideration of the following detailed description in conjunction with the drawings, in which:

FIG. 2 is a generalized flow chart of an arrhythmia recognition algorithm for the single chamber type of arrhythmia control device illustrated in FIG. 1;

FIG. 3 shows a block diagram for the classifier module of FIG. 1;

DETAILED DESCRIPTION OF THE INVENTION

Figure 1:
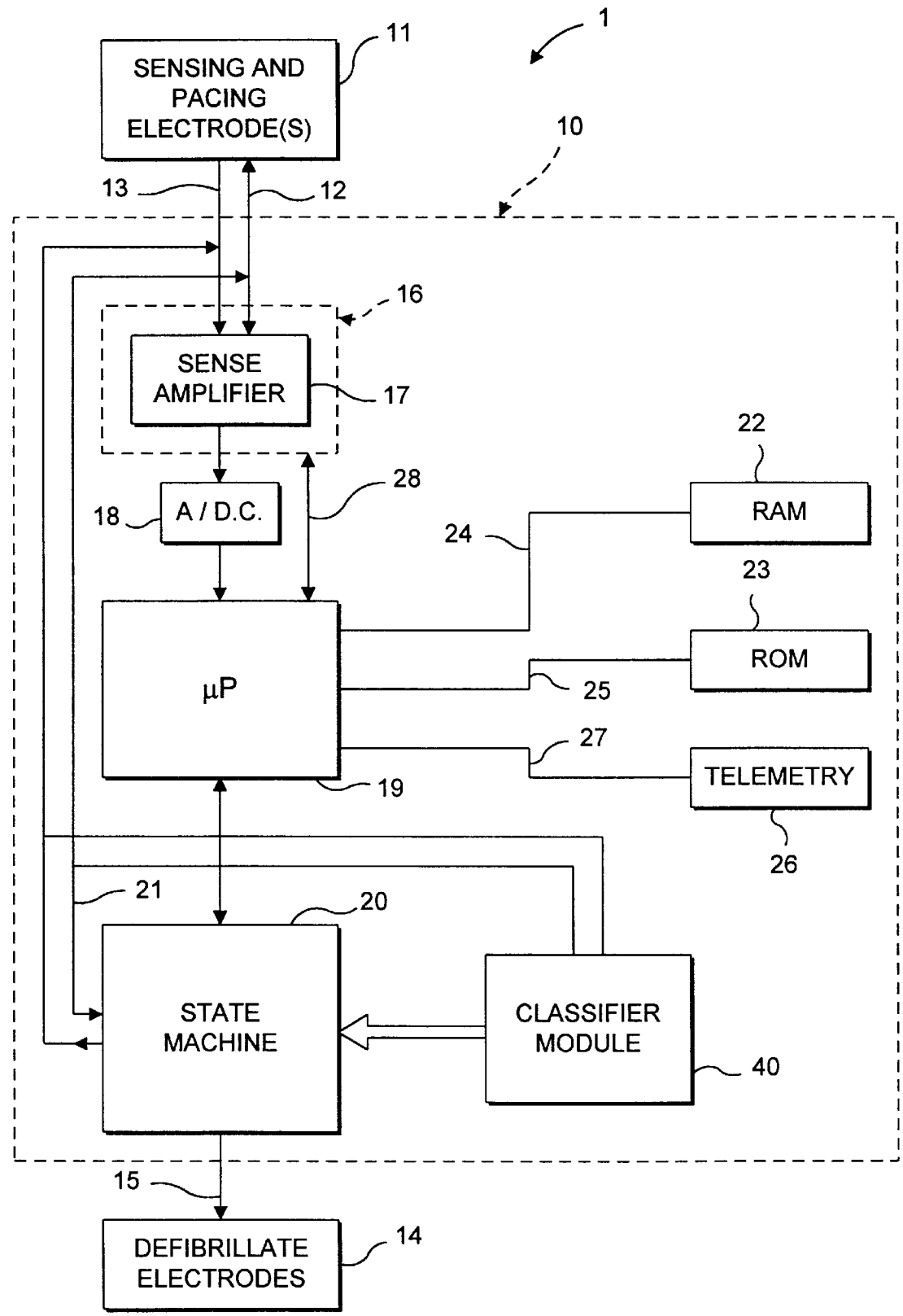
FIG. 1 is a block diagram of an arrhythmia control device in accordance with the present invention, which device may be either a single chamber or a dual chamber device.

With the exceptions noted below, the elements of FIG. 1 are described in U.S. Pat. No. 5,086,772 assigned to the assignee of the present invention. In that context, the present invention may be regarded as an improvement to the invention described therein. However, it is not intended that the invention be so limited. In fact, the present invention may be utilized with various other methods and apparatus as will be more fully appreciated by one skilled in the art after reference to the accompanying description. However, in order to describe the use of the invention in detail, the teachings of U.S. Pat. No. 5,086,772 are incorporated herein by reference. This includes a reference to an incorporation by reference of all the patent applications and/or patents described therein and incorporated by reference in U.S. Pat. No. 5,086,772.

Referring to FIG. 1, there is depicted a block diagram of an arrhythmia control device 1 which may be either a single chamber device or a dual chamber device. Device 1 is preferably designed to be implantable in a patient and includes a system module 10, one or more sensing and pacing electrodes, shown generally at 11, and appropriate leads 12 and 13 for connecting module 10 to the sensing electrodes 11. More particularly, when device 1 is a two chamber device, it generally includes an atrial sensing and pacing lead 12 extending to a corresponding one of the sensing and pacing electrodes 11 at the atrium of the patient's heart (not shown) for sensing atrial signals and administering pacing therapy to the atrium, and a ventricular sensing and pacing lead 13 extending to a corresponding one of the sensing and pacing electrodes at the ventricle of the patient's heart for sensing ventricular signals and administering pacing therapy to the ventricle. When device 1 is a single chamber device, the atrial sensing and pacing lead 12 and its associated sensing and pacing electrode are omitted from the device 1. In both cases the device 1 is further provided with one or more ventricular electrodes, shown generally at 14, for delivering defibrillation therapy to the ventricle of the heart, and suitable ventricular fibrillation leads 15 interconnecting the electrodes 14 and the system module 10.

Device 1 is further provided with sensing circuitry, shown generally at 16, which includes an amplifier 17 for amplifying the cardiac signals sensed by electrodes 11. The amplified cardiac signals outputted by amplifier 17 are fed to an analog-to-digital converter 18 which converts the cardiac signals to digital form and outputs the digital cardiac signals to a microprocessor, shown generally at 19, which, in response to various inputs received from other components of the module 10, performs various operations and generates various control and data outputs to a control module, shown generally at 20, which incorporates both pacemaking and defibrillating functions therein. Pacing therapy is delivered from the action module 20 to the atrial and ventricular sensing and pacing leads 11 and 12 by means of a bus, shown generally at 21. A suitable power supply (not shown), for example a battery in the case of an implantable device 1, is employed for the provision of reliable voltage levels to the various components of system module 10. A suitable end-of-life (EOL) signal line (not shown) is used to provide, to microprocessor 19, a logic signal indicative of the approach of battery failure in the power supply.

Microprocessor 19 is connected to a RAM unit 22 and to a ROM unit 23 by corresponding buses 24 and 25. Telemetry circuit 26, which is connected to microprocessor 19 by a bus 27, provides a bidirectional link between microprocessor 19 and an external device such as a programmer. It allows data such as the operating parameters to be read from or altered in the implanted system module 10.

State machine 20 preferably includes circuitry for selectively providing one or another of antitachycardia pacing, bradycardia pacing, defibrillation therapy and no therapy, upon command from microprocessor 19. In addition, when a two chamber device 1 is employed, the pacing therapy may be selectively provided to the atrium or ventricle, as called for by the microprocessor 19.

A classifier module 40 monitors the intrinsic cardiac activity and generates outputs to the state machine 20 for appropriate therapy. From a practical viewpoint, the control module 20 and classifier 40 are best implemented by software in the microprocessor 19, however they are shown here as separate elements for the sake of clarity.

In operation, sensing electrodes 11 detect atrial and ventricular analog signals from the heart. These signals are led to the sensing circuitry 16 on respective leads 12 and 13. In addition, the sensing circuitry 16 receives input atrial and ventricular sense control signals from microprocessor 19, via bus 28, which determine the sensitivity applied to the detection circuit. As more fully described below, a change in this sensitivity will affect the voltage deviation required at the sensing electrode for a sense to be registered. A logic arrangement which may be used to control changes in the sensitivity is described in greater detail in the U.S. Pat. No. 4,940,054 incorporated herein by reference.

Atrial and ventricular pace control circuits (not shown) are provided in the state machine 20 which cooperate with the microprocessor 19 to determine the respective types and magnitudes of atrial and ventricular pacing to occur. A logic arrangement which may be utilized to change the pulse energy is described in greater detail in the U.S. Pat. No. 4,869,252 incorporated herein by reference.

A suitable microprocessor 19 that may be used in connection with the present invention has been described in greater detail in the aforesaid U.S. Pat. No. 4,869,252 and is incorporated herein by reference. It comprises timers (not shown), a vectored interrupts block (not shown), a ROM 23, a RAM 22, an external memory (not shown), ports (not shown) and an internal communications bus (not shown). RAM 22 acts as a scratch pad and active memory during execution of the various programs stored in ROM 23 and used by microprocessor 19. These programs include system supervisory programs, the arrhythmia recognition algorithm forming one of the main features of the present invention, to be described in greater detail hereinafter, and storage programs for storing, in external memory, data concerning the functioning of module 10 and the electrogram (EGM) provided by ventricular sensing and pacing lead 13. Signals received from telemetry circuit 26 permit an external programmer (not shown) to change the operating parameters of state machine 20 by supplying appropriate signals to microprocessor 19.

Referring now to FIG. 2, a generalized flow chart for an arrhythmia recognition algorithm for an implantable single chamber arrhythmia control device is illustrated. Although described herein in connection with a single chamber implantable arrhythmia control device, this algorithm may be used with externally located arrhythmia control devices which do not employ implanted sensing electrodes, and which apply high electrical energy defibrillation pulses to the external portion of a patient's chest. It is also applicable to externally located devices which are connected to electrodes implanted within the patient's chest.

Resuming consideration of FIG. 2, the starting point of the algorithm is shown at 100. Upon start-up of the device 1, the algorithm proceeds through a four second initialization step, shown at 101, during which normal sinus rhythm (NSR) data of the patient is analyzed to determine an event threshold level and to establish the morphology of an average normal sinus rhythm R-wave. The morphological features determined may include for example the polarity of the R-wave and its duration or R-wave width. The algorithm is then initialized to start viewing data for rhythm analysis, as shown at 102. (The NSR event threshold level and morphology are periodically updated during operation of the device 1.)

At this point, the algorithm proceeds to its event and peak detection step or phase, shown at 103, wherein incoming electrogram (EGM) data analysis begins and event and peak detection of R-waves occur. Once the time of occurrence of the peak of the R-wave has been determined at 103, R-wave peak-to-peak interval calculations and R-wave morphology calculations are performed, at step 104.

The R-wave peak-to-peak interval and R-wave morphology calculation information developed at step 104 is then utilized in the event classification portion of the algorithm, at step 105. During event classification, each of the particular events are classified into one or another of several events including: (i) a potential bradycardia event; (ii) a potential non-pathological event; (iii) a potential ventricular tachycardia (VT) event; (iv) a potential ventricular fibrillation (VF) event and (v) a noise event. In this classification scheme, if a potential supraventricular tachycardia (SVT) beat is preset, it is placed in the potential non-pathological event classification category. The foregoing event classification information is then utilized in the rhythm classification portion of the algorithm, at step 106.

The circuitry and steps for performing the event classification (step 105) in accordance with the present invention is now described. Referring first to FIG. 3, the atrial sense signal is first fed to sense amplifier 117 which may or may not be the same as amplifier 17 (FIG. 1). The output of amplifier 117 is fed to a ventricular sense detector 118 which may use a dynamically adjusted threshold to detect proper intrinsic atrial pulses, as described for example in U.S. Pat. No. 5,395,393, incorporated herein by reference. The output of this detector 118 is fed to an interval timer 120 as well as a noise detector 122 and a class selector 124. The classifier module 40 then uses certain preselected rules, defined more fully below to classify the ventricle as having one of the following conditions: NSR (normal sinus rate), VT (ventricular tachycardia), VF (Ventricular fibrillation), or noisy. This information is passed on to the state machine 20. In response, the state machine 20 generates appropriate control signals for the microprocessor 19 to generate an appropriate therapy (if any). A suitable noise detector is described for example in U.S. Pat. No. 4,960,123.

Figure 4:
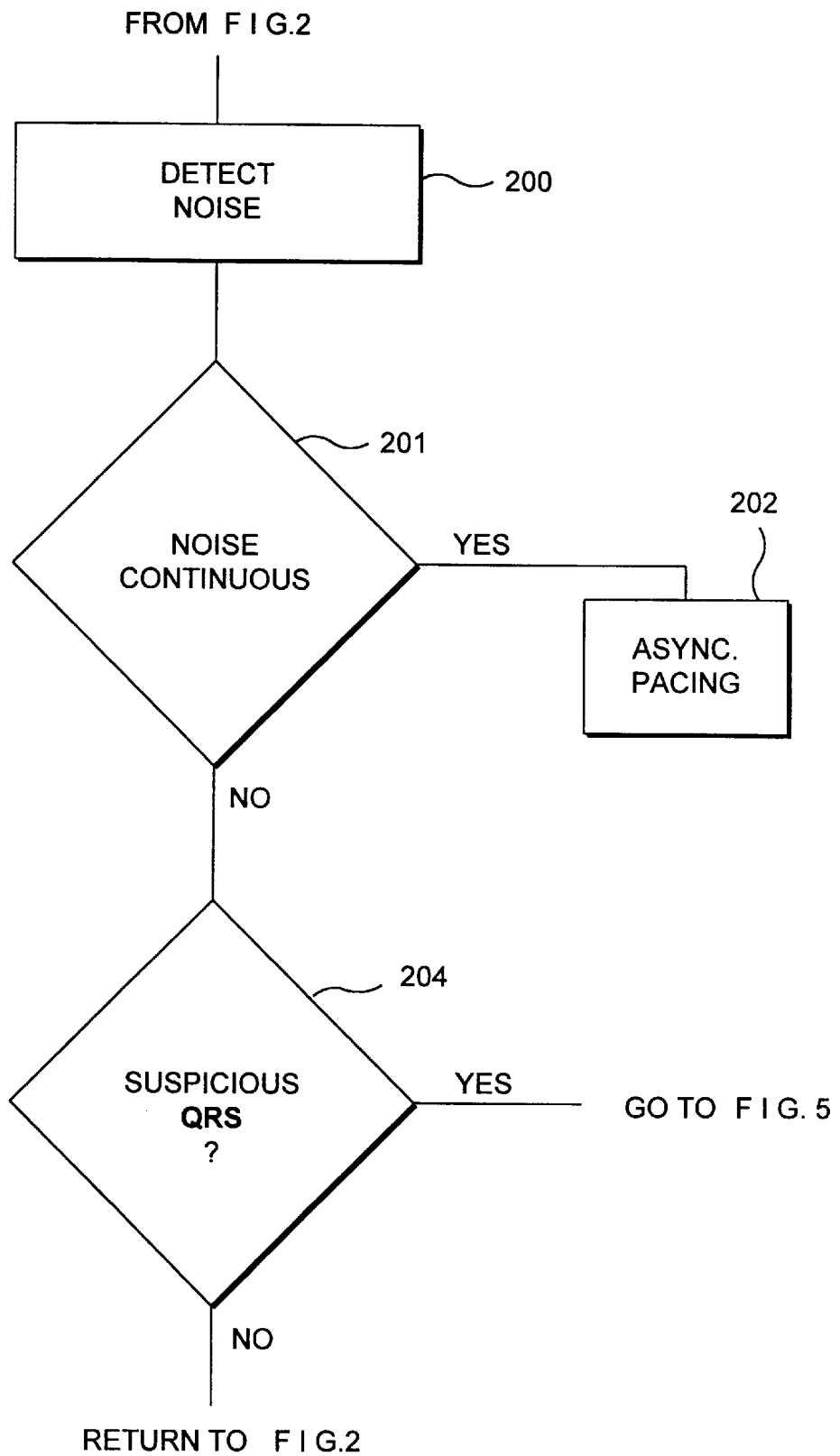
FIGS. 4 and 5 are flow charts showing in greater detail the steps related to event classification, rhythm classification and appropriate therapy.
Figure 5:
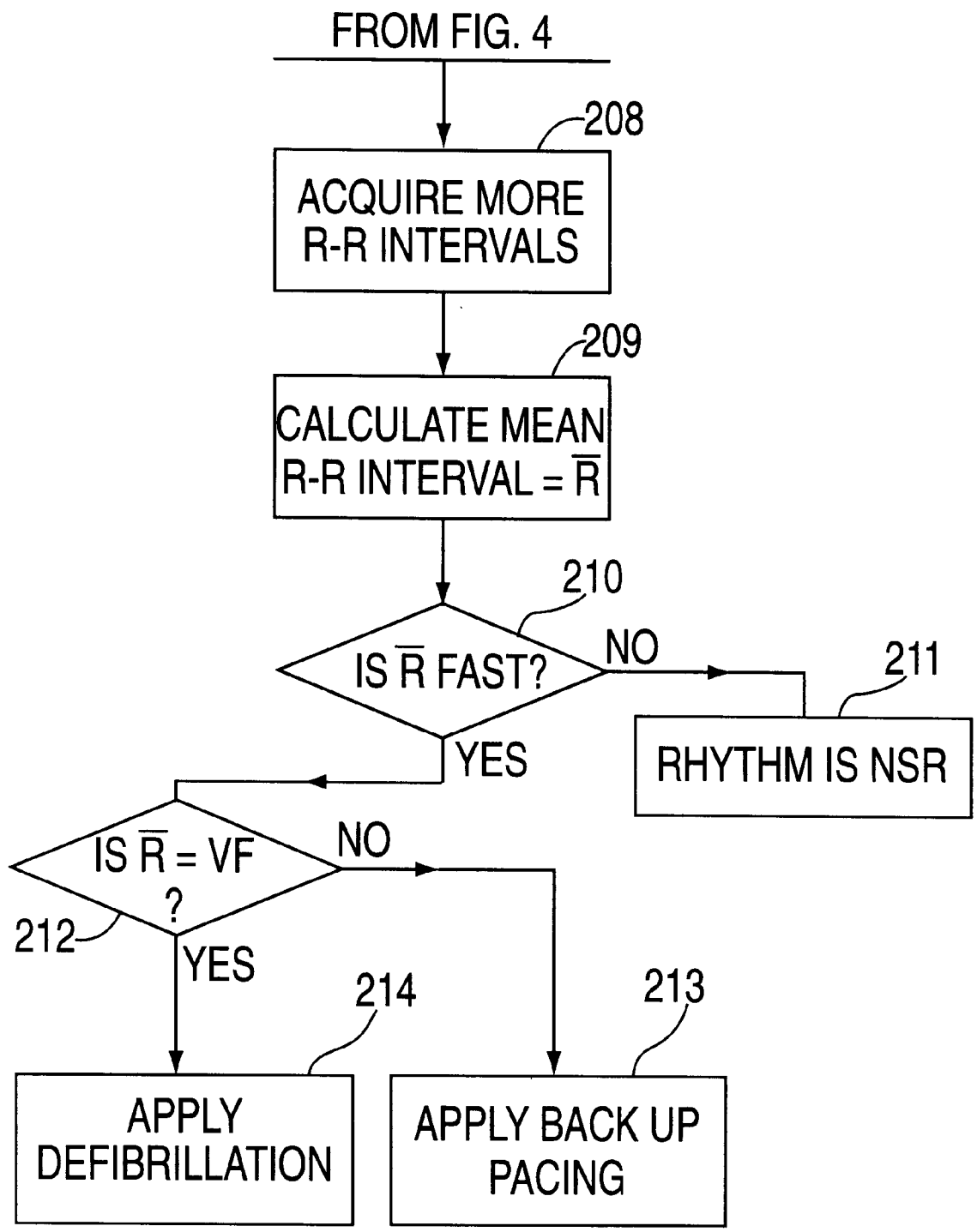

The operation of the circuitry of FIG. 3 is now described in conjunction with the flow charts of FIGS. 4-5. Starting in FIG. 4, with step 200, the noise detector 122 is first used to detect noise from the electrodes. The class selector 124 then must determine if a constant or continuous noise condition exists, i.e., whether the noise detector 122 detects noise continuously (step 201) for a predetermined amount of time, rather than intermittently. If the noise is continuously sensed, then the class selector generates a NOISE signal to the state machine which then starts pacing the heart asynchronously (for example in a VOO mode), i.e., independently of the sensed signal either for a predetermined amount of time, or until the noise condition is no longer sensed (step 202).

If a noise signal is detected but it is intermittent, then in step 204 a determination is made by the class selector 124 as to whether the detected QRS complex is suspicious. The QRS complex may be suspicious, for example, if its peak amplitude is very low. A low peak amplitude may be, for instance, 3 mv.

A low amplitude QRS complex under these conditions is less likely to be ventricular tachycardia. It may indicate a poor electrode connection to the heart or may indicate the presence of noise or another artifact. Accordingly in step 208, a larger number of heart beats is sensed to get a more consistent measurement of heart rate to improve the rhythm classification with the lower quality QRS complexes. Then in step 209, a mean heart interval is calculated, and in step 210, this mean interval is compared to a threshold to determine whether it is still a fast heart rate.

If the mean heart rate is not fast, it is classified as normal in step 211 and monitored for any further irregularities as in step 103.

If the mean heart rate is very fast and consistent with ventricular fibrillation (in step 212), it is better to apply defibrillation therapy (step 214) even though the signal is of poor quality. This is because the risk of not treating ventricular fibrillation is that the patient will probably die.

However, if the rate is not consistent with VF (step 212) it may be safer not to deliver any aggressive antitachycardia therapies as they may induce a tachycardia where there is not one. In this situation it is safer to deliver backup pacing for bradycardia as the poor signal quality may be due to noise or other artifact.

More particularly, if the interval R is consistent with ventricular fibrillation (R>300 msec) (step 214) then in step 214 antifibrillation therapy, (i.e., shocks) is applied. Otherwise NSR is assumed.

In this manner, the classifier circuit 40 acts as a reliability detector for detecting the reliability of the sensed QRS complex. More particularly, circuit 40 develops a quality indicator for the QRS complex. A noisy and suspicious (i.e. low) QRS complex is followed by a modified antitachycardia therapy and no antifibrillation is applied since the later is very unlikely. This mode is prescribed for a predetermined period of time during which a more precise classification can be made.

Otherwise normal QRS and Rhythm classification is followed and normal therapy is applied (if any).

Although the invention has been described using signal amplitude and noise amplitude as the indicators of signal quality and reliability, it is to be understood that these are merely illustrative of the application of the principles of the invention. Accordingly, other measures may be used by the invention to indicate signal quality in further embodiments of this invention.

Although the invention has been described with reference to several particular embodiments, it is to be understood that these embodiments are merely illustrative of the application of the principles of the invention. Accordingly, the embodiments described in particular should be considered exemplary, not limiting, with respect to the following claims.

I claim:

1. An implantable pacemaker comprising:
   a sensor for sensing intrinsic events in a patient's heart;
   a classifier classifying said events into one of several groups and generating control signals corresponding to a respective one of said groups, said control signals defining a therapy appropriate to each of said group;
   a reliability detector determining a reliability of said classifier, said reliability detector generating an indication if said reliability detector determines that said classifier made an unreliable classification; and
   a pulse generator receiving said control signals and said indication and generating in response first therapeutic rules in the presence of said indication and second therapeutic rules in the absence of said indication;

wherein said reliability detector includes a noise sensor for detecting noise from said sensor, a feature extractor for extracting an event feature of sensed events in the presence of noise; and a comparator for comparing said event feature to a threshold, said indication being generated based on the comparison.

2. A pacemaker for implantation in a patient, said pacemaker comprising:

a sensor sensing a cardiac event and generating a sensed signal;

a pulse generator for generating therapeutic pulses in response to commands;

a classifier classifying a condition of the patient's heart based on said sensed signal and generating a corresponding therapy signal;

a reliability detector detecting a reliability of said therapy signal; and generating a reliability indication; and a controller receiving said therapy signal and said reliability indication and generating said commands.

3. The pacemaker of claim 2 wherein said reliability detector includes a noise sensor detecting noise from said sensor.

4. The pacemaker of claim 3 wherein said reliability detector further includes an analyzer for analyzing said sensed signal in the presence of noise.

5. The pacemaker of claim 4 wherein said analyzer includes means for determining whether said sensed signal meets a preselected criteria, and it so, generating said reliability indication.

6. The pacemaker of claim 3 wherein said reliability detector includes a noise timer to determine if said noise is continuous.

7. The pacemaker of claim 6 wherein said reliability detector is adapted to generate said reliability indication in the presence of continuous noise.

8. The pacemaker of claim 3 wherein said pulse generator includes means for generating pacing pulses.

9. The pacemaker of claim 3 wherein said pulse generator includes means for generating defibrillation pulses.

10. The pacemaker of claim 3 where said reliability detector includes means for measuring a signal amplitude or morphology.

11. The pacemaker of claim 3 where said reliability detector includes means for classifying a low signal amplitude as a low quality signal.

12. The pacemaker of claim 3 where said controller is adapted to acquire more input signals for an improved rhythm classification if the said reliability detector indicates a low signal quality.

13. The pacemaker of claim 3 where said controller selects a safer form of therapy if the said reliability detector indicates a low signal quality.

14. A method of applying cardiac therapy to a patient using an implantable device comprising the steps of:

sensing a cardiac event and generating a response to a sense signal;

sensing a noise signal associated with said cardiac event;

classifying said sense signal as a first cardiac condition in the absence of noise;

analyzing said sensed signal in the presence of noise to determine if center preselected criteria are met;

classifying said sense signal as a second condition in the presence of said criteria; and applying therapeutic pulses in accordance with all of said first and second conditions.

15. The method of claim 10 further comprising detecting if said noise is continuous.

* * * * *